(12) United States Patent
Lai

(10) Patent No.: US 6,783,505 B1
(45) Date of Patent: Aug. 31, 2004

(54) HIGH-PRESSURE WATER-SPRAY DEVICE FOR CLEANING TEETH

(76) Inventor: Cheng-Fu Lai, No. 5-1, Lane Chyi Parn Gou Chyan Li, Lukang Cheng, Changhwa Hsien (TW)

(*) Notice: Subject to any disclaimer, the term of this patent is extended or adjusted under 35 U.S.C. 154(b) by 114 days.

(21) Appl. No.: 10/320,785

(22) Filed: Dec. 17, 2002

(51) Int. Cl.$^7$ .............................................. A61H 13/00
(52) U.S. Cl. .............................. 601/162; 433/88; 4/615
(58) Field of Search .................... 433/80, 88; 601/154, 601/155, 132, 165; 4/615; 239/444, 445

(56) References Cited

U.S. PATENT DOCUMENTS

| | | | | |
|---|---|---|---|---|
| 1,646,942 A | * | 10/1927 | Tuorto | 433/88 |
| 2,867,230 A | * | 1/1959 | Bletcher et al. | 4/615 |
| 3,500,824 A | * | 3/1970 | Gilbert | 601/165 |
| 3,771,517 A | * | 11/1973 | Radecki | 601/165 |
| 3,973,558 A | * | 8/1976 | Stouffer et al. | 601/165 |
| 4,752,975 A | * | 6/1988 | Yates | 4/601 |
| 5,934,902 A | * | 8/1999 | Abahusayn | 433/80 |

* cited by examiner

*Primary Examiner*—Todd E. Manahan
(74) *Attorney, Agent, or Firm*—Charles E. Baxley

(57) ABSTRACT

A high-pressure water-spray device is used to clean the teeth and is formed of a faucet connector, and a rotary member rotatably fastened to the faucet connector and provided with a receiving slot for receiving rotatably a flow control valve, and a locating slot for rotatably positioning a spherical water-spray member. The locating slot is in communication with the receiving slot which is in turn in communication with the faucet connector via a water channel of the rotary member. The flow control valve is rotatably disposed in the receiving slot in conjunction with a confinement ring. The water-spray member is rotatably disposed in the locating slot in conjunction with a stop ring.

4 Claims, 6 Drawing Sheets

HIGH-PRESSURE WATER-SPRAY DEVICE FOR CLEANING TEETH

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates generally to an oral hygiene device, and more particularly to a high-pressure water-spray device for cleaning the teeth.

BACKGROUND OF THE INVENTION

The toothbrush is generally used to clean the teeth; however it is difficult to reach certain areas of the mouth. In addition, the toothbrush cannot remove effectively and thoroughly bits of food from the space between the teeth. The dentist often uses a high-pressure water-spray device to clean the teeth of a person under treatment. However, such a dental device is designed for use exclusively by the dentist or dental assistant.

BRIEF SUMMARY OF THE INVENTION

The primary objective of the present invention is to provide a high-pressure water-spray device which is designed for use by an individual to clean his or her own teeth.

The device of the present invention comprises a faucet connector and a high-pressure water-spray unit which is formed of a fastening member, a rotary member, a water-spray member, and a flow adjusting valve. The device of the present invention can be connected to a faucet for cleaning the teeth of a person. The device can be turned in all directions so as to enable the water jet stream to reach all areas of the mouth.

The features, functions, and the advantages of the present invention will be more readily understood upon a thoughtful deliberation of the following detailed description of a preferred embodiment of the present invention with reference to the accompanying drawings.

DETAILED DESCRIPTION OF THE INVENTION

Figure 1:
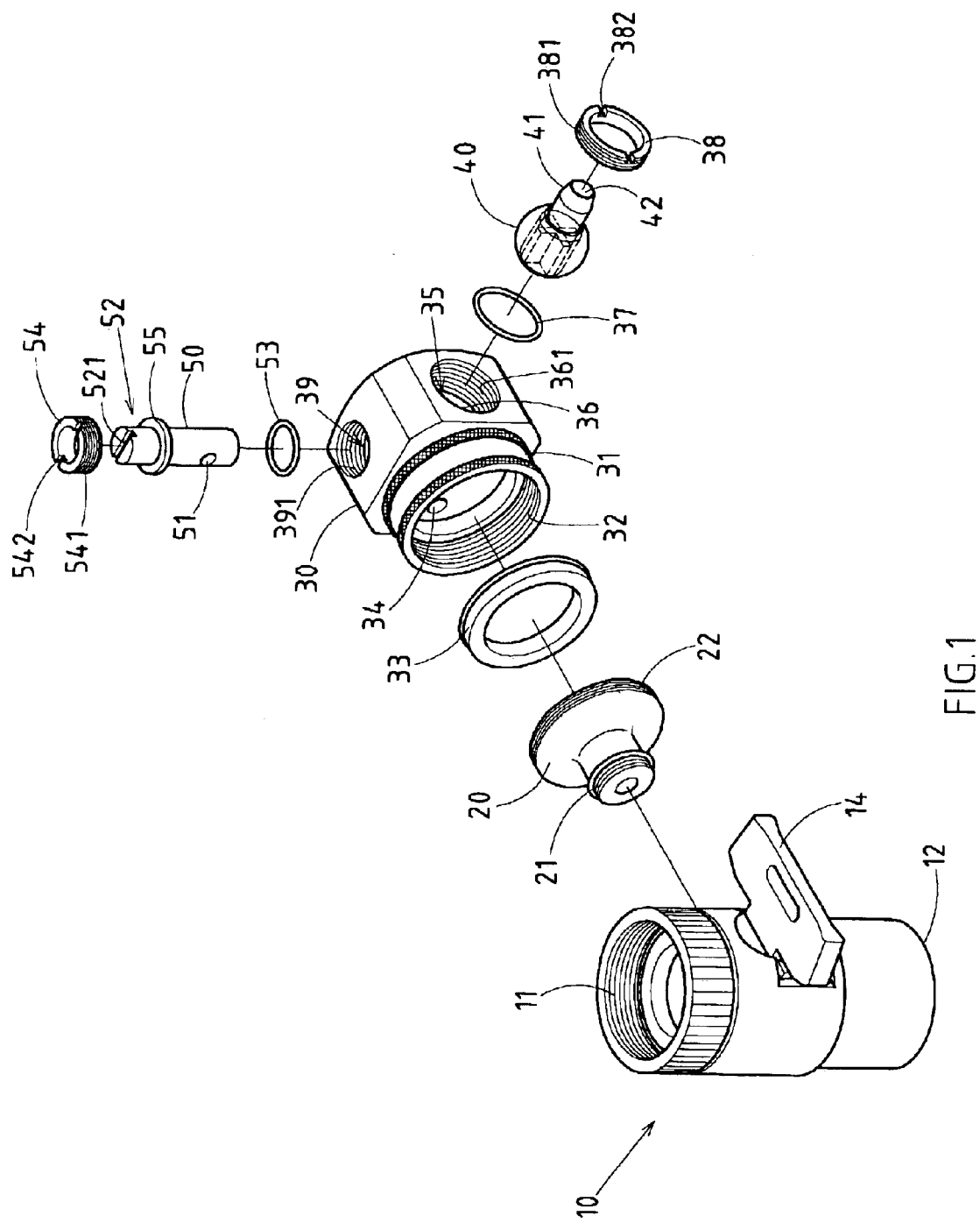
FIG. 1 shows an exploded perspective view of the preferred embodiment of the present invention.
Figure 2:
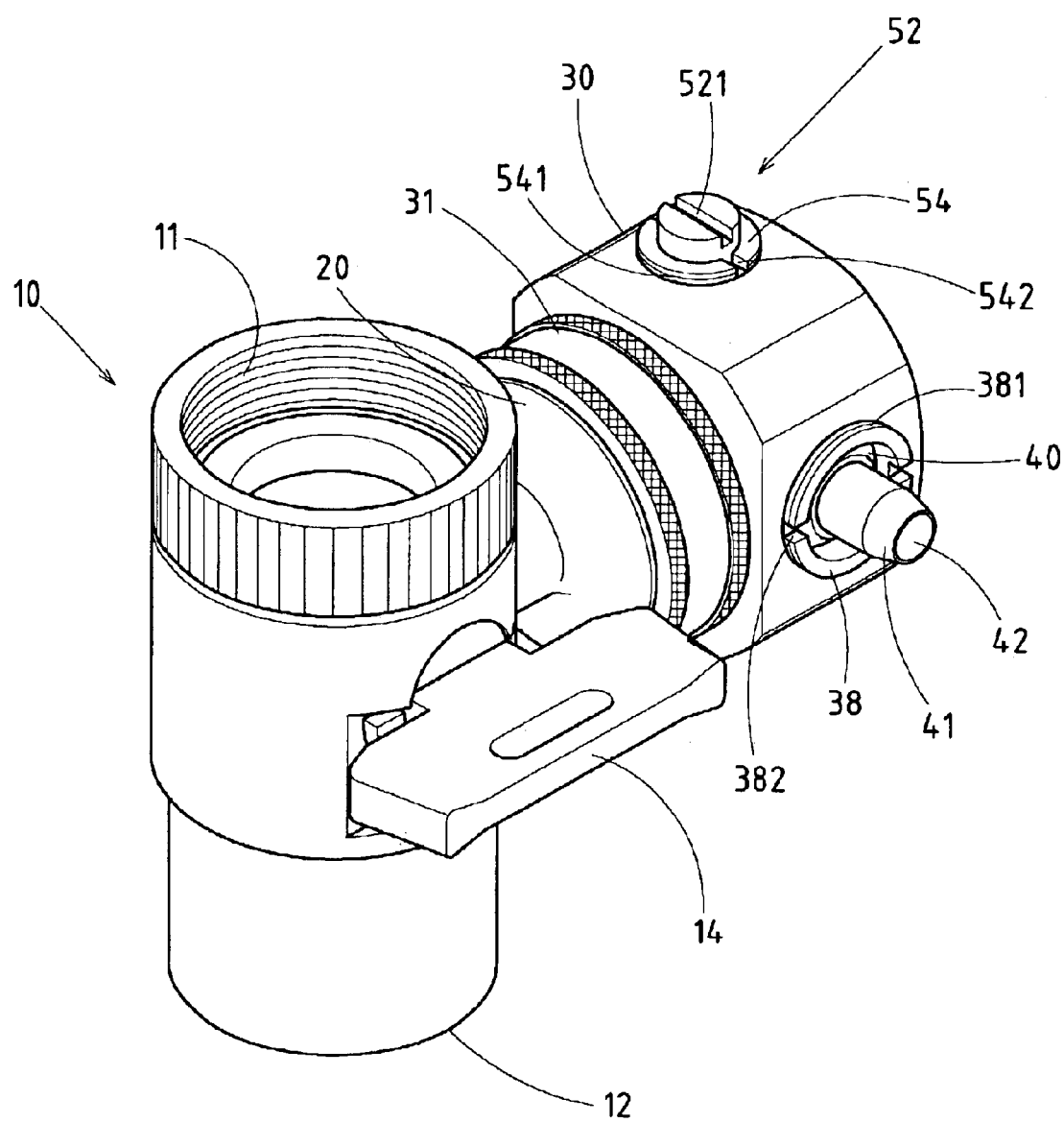
FIG. 2 shows a perspective view of the preferred embodiment of the present invention.
Figure 3:
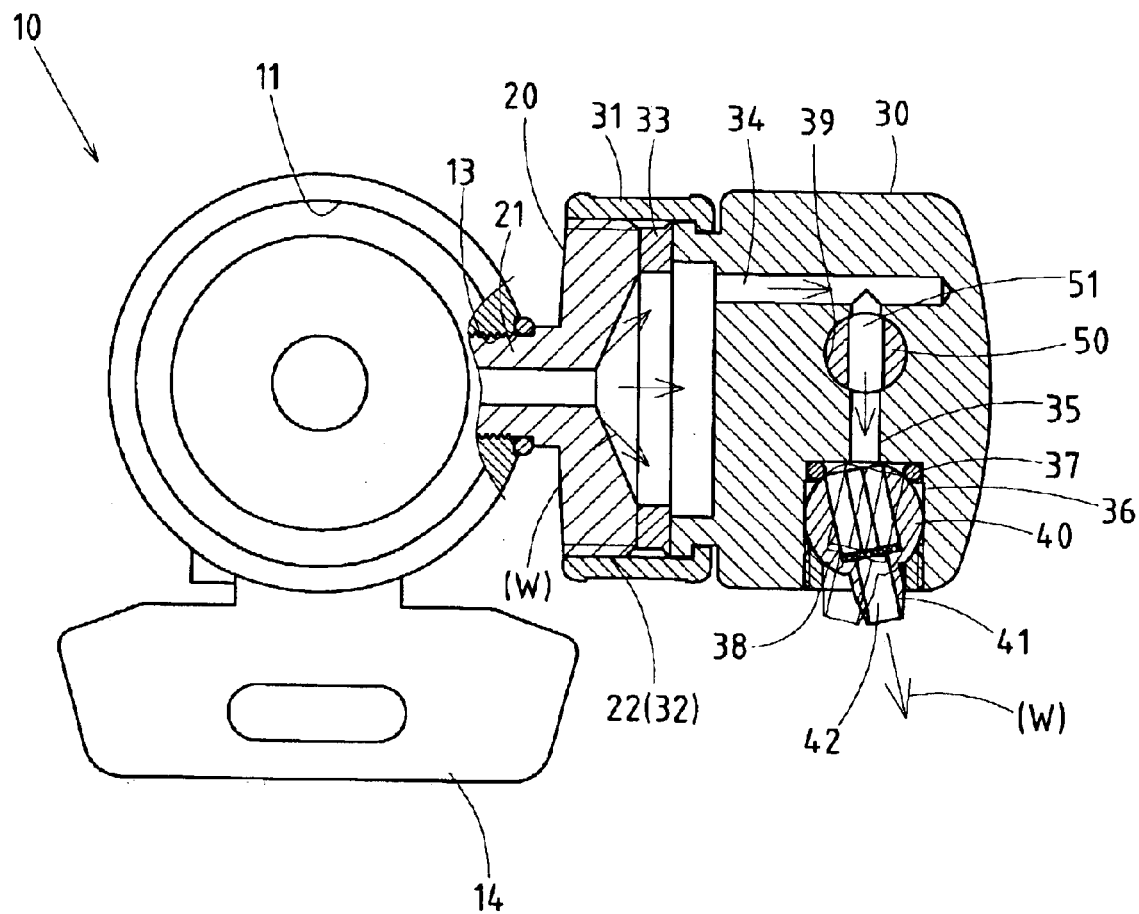
FIG. 3 is a sectional schematic view of the preferred embodiment of the present invention to show the angular adjustment of the water jet stream.
Figure 4:
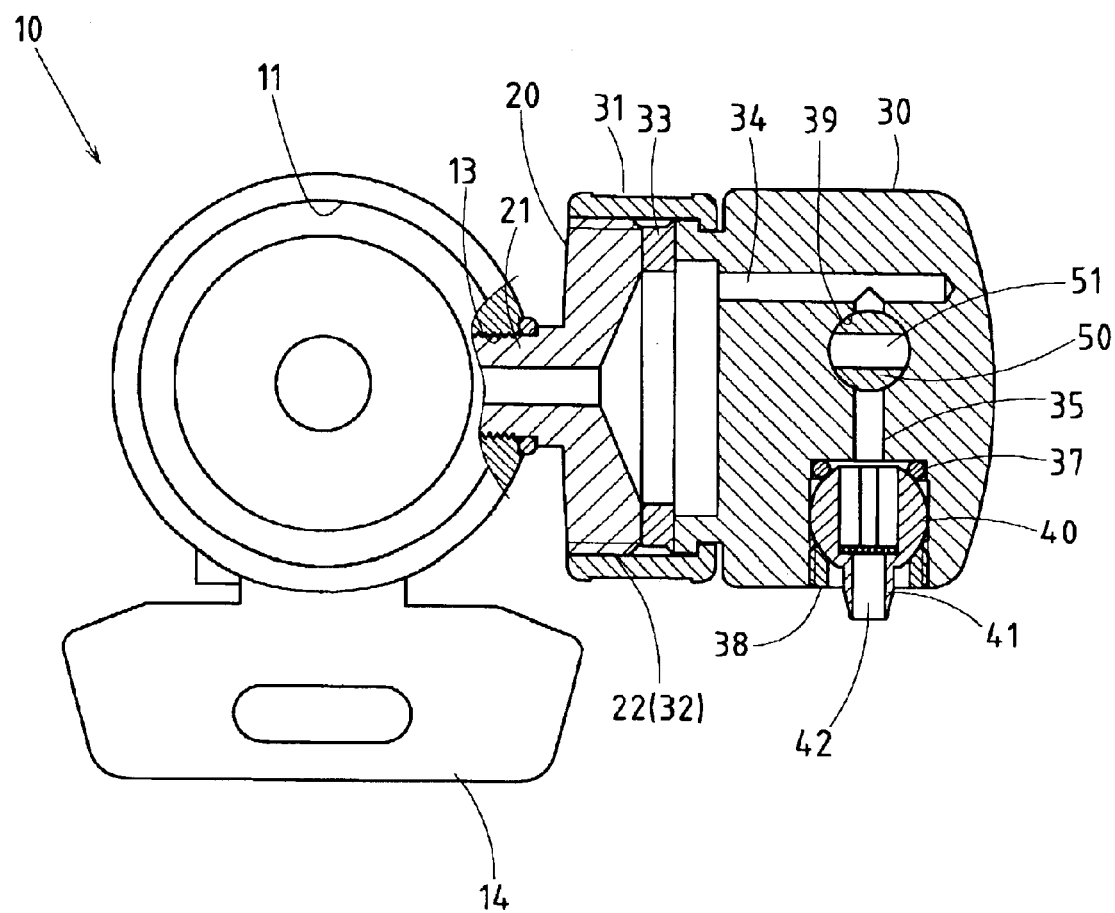
FIG. 4 is a sectional schematic view to show the flow control mechanism of the preferred embodiment of the present invention.
Figure 5:
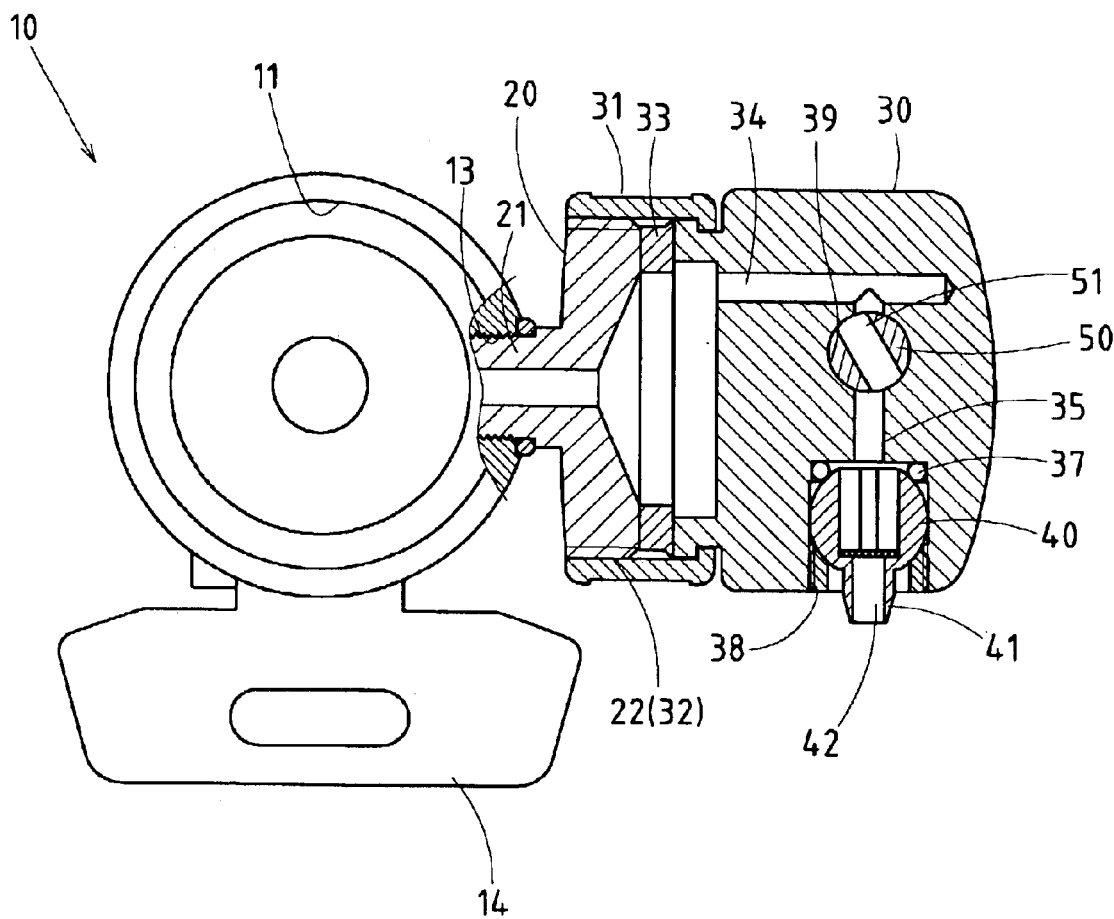
FIG. 5 is a sectional schematic view to show the flow stoppage mechanism of the preferred embodiment of the present invention.
Figure 6:
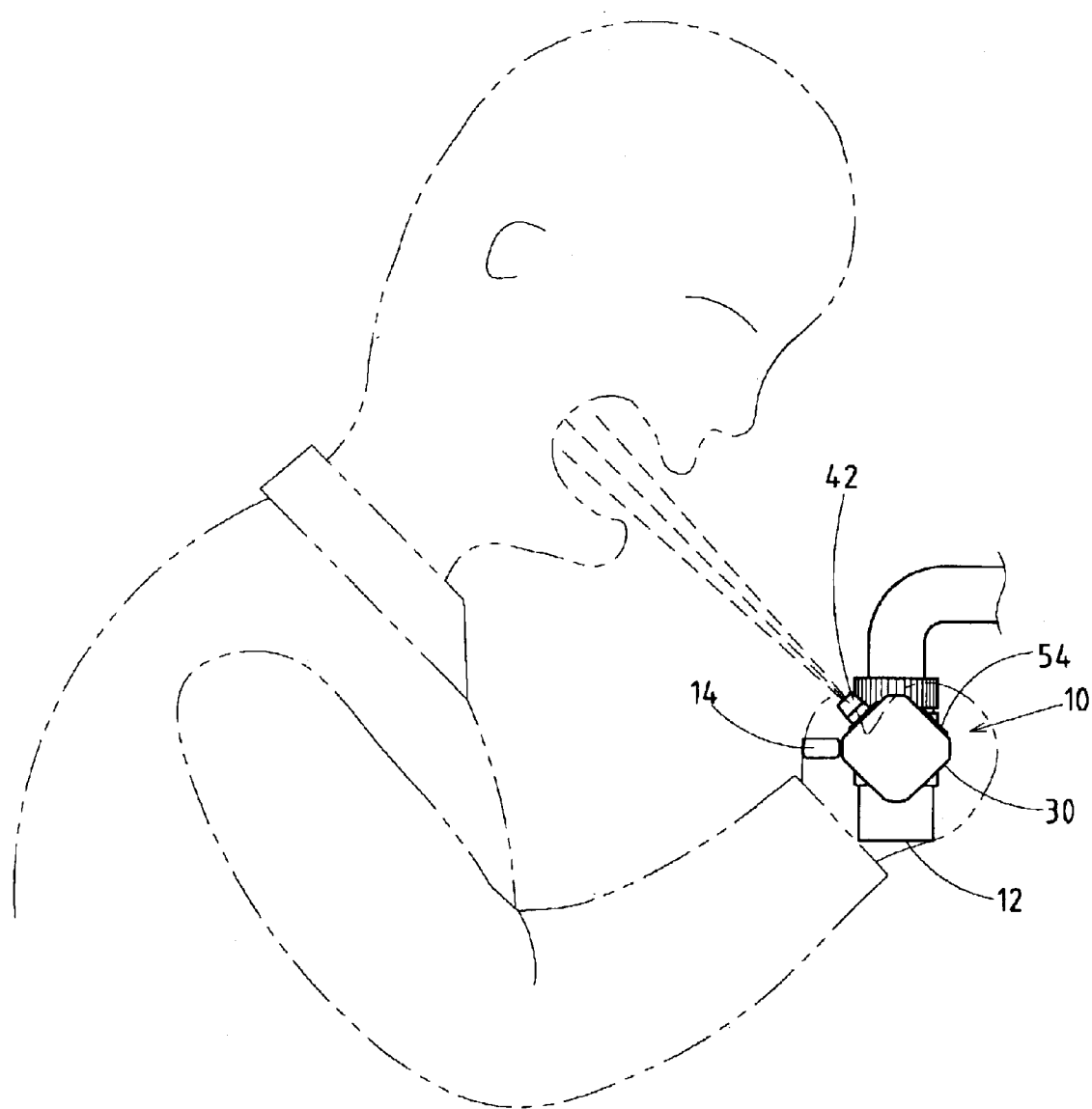
FIG. 6 shows a schematic view of the preferred embodiment of the present invention in use.

As shown in FIGS. 1–6, a high-pressure water-spray device embodied in the present invention comprises a faucet connector 10, a fastening member 20, a rotary member 30, a water-spray member 40, and a flow control valve 50.

The faucet connector 10 is of a hollow cylindrical construction and is provided at one end with a connection portion 11 engageable with a faucet (not shown in the drawings). The faucet connector 10 is provided at other end with a water discharge hole 12, and in a longitudinal side wall with a water output hole 13. The discharge of water can be controlled by a control piece 14.

The rotary member 30 is provided with a rotary water inlet 31, which is fastened with a connection end 22 of the fastening member 20 is conjunction with a washer 33. The fastening member 20 has a fastening end 21 which is fastened with the water output hole 13 of the faucet with the water output hole 13 of the faucet connector 10. The water inlet 31 is provided with an inner threaded portion 32 which is fastened with the connection end 22 of the fastening member 20. The rotary member 30 is provided in an interior with an L-shaped water channel 34 in communication with the rotary water inlet 31. The rotary member 30 is further provided in the interior with a waterspray hole 35 in communication with the water channel 34. The water-spray hole 35 is provided with a locating slot 36 for locating a washer 375 and a stop ring 38. The water-spray member 40 is provided with a barrel 41 having a jet nozzle 42. The rotary member 40 is rotatably disposed in the locating slot 36 in conjunction with the washer 37 and the stop ring 38. The water-spray member 40 is confined by the stop ring 38; nevertheless it is capable of turning in all directions. The locating slot 36 is provided with an inner threaded portion 361, while the stop ring 38 is provided with an outer threaded portion 381. The stop ring 38 is located in the locating slot 36 such that the outer threaded portion 381 is engaged with the inner threaded portion 361 of the locating slot 36. It must be noted here that the water-spray member 40 is of a spherical construction. Accordingly, the locating slot 36 is similar in profile to the water-spray member 40. The stop ring 38 is provided with a slotted end 382 to facilitate the turning of the stop ring 38 by a screwdriver.

The rotary member 30 is further provided with a receiving slot 39 in communication with the water channel 34. The receiving slot 39 is used to receive rotatably the flow control vale 50 in conjunction with a washer 53 and a confinement ring 54. The flow control valve 50 is provided with a through hole 51, a turning portion 52, and an annular projection 55 located between the through hole 51 and the turning portion 52. The confinement ring 54 is rested on the projection 55 such that an outer threaded portion 541 of the confinement ring 54 is engaged with an inner threaded portion 391 of the receiving slot 39 of the rotary member 30. The flow control valve 50 is turned by the turning portion 52 so as to enable the through hole 51 to be aligned with the water channel 34 of the rotary member 30. The turning portion 52 is provided with a slotted top end 521 to facilitate the turning of the turning portion 52 by a screwdriver.

The confinement ring 54 is provided with a slotted top end 54 to facilitate the turning of the confinement ring 54 by a screwdriver.

The embodiment of the present invention described above is to be regarded in all respects as being illustrative and nonrestrictive. Accordingly, the present invention may be embodied in other specific forms without deviating from the spirit thereof. The present invention is therefore to be limited only by the scope of the following claims.

I claim:

1. A high-pressure water-spray device for cleaning teeth, said device comprising:

a faucet connector of a hollow cylindrical construction and provided at one end with a connection portion engageable with a faucet, said faucet connector further provided at another end with a water discharge hole controlled by a control piece, and in a longitudinal side wall with a water output hole;

a fastening member fastened at a fastening end to said water output hole of said faucet connector and comprised of a connection end; and a rotary member comprised of a rotary water inlet which is engaged with said connection end of said fastening member, said rotary member further comprised of, in an interior, a water channel in communication with said rotary water inlet, a receiving slot in communication with said water channel, a flow control valve rotatably received in said receiving slot, a locating slot in communication with said receiving slot, and a water-spray member rotatably received in said locating slot;

wherein said receiving slot is comprised of an inner threaded portion, said flow control valve being comprised of a through hole, a turning portion, and an annular projection, said flow control valve being rotatably fastened in said receiving slot in conjunction with a confinement ring, to said confinement ring being comprised of an outer threaded portion which is engaged with said inner threaded portion of said receiving slot such that said confinement ring is stopped by said annular projection of said flow control valve whereby said flow control valve is turned by an external force exerting on said turning portion, so as to align said through hole of said flow control valve with said water channel of said rotary member; and wherein said locating slot is of a spherical construction and is comprised of an inner threaded portion, said water-spray member corresponding in form to said locating slot and being comprised of a jet nozzle whereby said water-spray member is rotatably located in said locating slot in conjunction with a stop ring which is comprised of an outer threaded portion that is engaged with said inner threaded portion of said locating slot.

2. The high-pressure water-spray device as defined in claim 1, wherein said turning portion of said flow control valve is comprised of a slotted end to facilitate turning of said flow control valve by a screwdriver.

3. The high-pressure water-spray device as defined in claim 1, wherein said confinement ring is comprised of a slotted end to facilitate turning of said confinement ring by a screwdriver.

4. The high-pressure water-spray device as defined in claim 1, wherein said stop ring is comprised of a slotted end to facilitate turning of said stop ring by a screwdriver.

* * * * *